(12) United States Patent
Hiraide et al.

(10) Patent No.: US 7,056,968 B2
(45) Date of Patent: *Jun. 6, 2006

(54) CALCIUM PHOSPHATE-SYNTHETIC RESIN COMPOSITE BODY CONTAINING CALCIUM PHOSPHATE BLOCK AND METHOD FOR PRODUCTION THEREOF

(75) Inventors: Tsuneo Hiraide, Saitama-ken (JP); Yukio Kubota, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 46 days.

This patent is subject to a terminal disclaimer.

(21) Appl. No.: 10/615,013

(22) Filed: Jul. 9, 2003

(65) Prior Publication Data

US 2004/0096475 A1 May 20, 2004

(30) Foreign Application Priority Data

Jul. 9, 2002 (JP) ............................. 2002-200085

(51) Int. Cl.
*C08K 3/32* (2006.01)

(52) U.S. Cl. ............... 524/414; 524/436; 524/417; 524/706; 523/506; 428/307.3; 428/327; 424/423

(58) Field of Classification Search ............ 428/307.3, 428/327; 523/200, 300, 506; 524/417, 706, 524/415, 436, 414; 424/423
See application file for complete search history.

(56) References Cited

U.S. PATENT DOCUMENTS

| | | | |
|---|---|---|---|
| 3,787,900 A | | 1/1974 | McGee |
| 4,192,021 A | * | 3/1980 | Deibig et al. ............. 623/23.61 |
| 4,222,128 A | * | 9/1980 | Tomonaga et al. ........ 623/23.51 |
| 4,456,723 A | * | 6/1984 | Breitenfellner et al. ..... 524/415 |
| 4,818,451 A | | 4/1989 | Arai et al. |
| 4,904,534 A | * | 2/1990 | Nagai ......................... 428/457 |
| 2004/0071954 A1 | * | 4/2004 | Hiraide et al. .............. 428/327 |

FOREIGN PATENT DOCUMENTS

| | | |
|---|---|---|
| EP | 205333 | 12/1986 |
| EP | 962215 | 12/1999 |
| GB | 2010095 | 6/1979 |
| GB | 2216013 | 10/1989 |

(Continued)

OTHER PUBLICATIONS

English Language Abstract of JP Appln. No. 02-167868.

(Continued)

*Primary Examiner*—David W. Wu
*Assistant Examiner*—Satya Sastri
(74) *Attorney, Agent, or Firm*—Greenblum & Bernstein, P.L.C.

(57) ABSTRACT

A calcium phosphate-synthetic resin composite body produced by pressing a calcium phosphate block (or a calcium phosphate block and calcium phosphate particles), and synthetic resin particles I, which are at least partially cross-linked in advance, and uncross-linked, synthetic resin particles II while heating, the calcium phosphate block being exposed on at least part of the surface of the composite body. The above composite body is produced by a method comprising the steps of (a) introducing the calcium phosphate block (or a calcium phosphate block and calcium phosphate particles), the synthetic resin particles I and II into a cavity of a forming die such that the calcium phosphate block is present on at least part of the surface of the composite body, and that the synthetic resin particles surround the calcium phosphate particles, if any; and (b) pressing them in the cavity of the forming die while heating, so that the synthetic resin particles are bonded to each other.

26 Claims, 8 Drawing Sheets

FOREIGN PATENT DOCUMENTS

| | | |
|---|---|---|
| GB | 2391833 | 2/2004 |
| IE | 920833 | 3/1992 |
| JP | 63279835 | 11/1988 |
| JP | 2-167868 | 6/1990 |
| JP | 02167868 | 6/1990 |
| JP | 05277174 A * | 10/1993 |
| JP | 06105901 A * | 4/1994 |
| JP | 8-48583 | 2/1996 |
| JP | 08048583 | 2/1996 |
| JP | 2002-265795 | 9/2002 |
| JP | 02265795 | 9/2002 |
| JP | 2004-018459 | 1/2004 |
| JP | 2004-222806 | 8/2004 |

OTHER PUBLICATIONS

English Language Abstract of JP Appln. No. 08-048583.
English Language Abstract of JP Appln. No. 2002-265795.
English Language Abstract of JP 2004-222806.
English Language Abstract if JP 2004-018459.

* cited by examiner

CALCIUM PHOSPHATE-SYNTHETIC RESIN COMPOSITE BODY CONTAINING CALCIUM PHOSPHATE BLOCK AND METHOD FOR PRODUCTION THEREOF

BACKGROUND OF THE INVENTION

The present invention relates to a calcium phosphate-synthetic resin composite body having excellent workability, impact resistance and water resistance as well as high biocompatibility, and a method for the production thereof.

Calcium phosphate is utilized for biomaterials such as artificial dental roots, bone reinforcements and dental cements because of excellent biocompatibility. However, it is poor in toughness due to its nature as a ceramic and cannot be used for members requiring impact resistance. Thus, artificial dental roots and bone reinforcements are made of metallic materials, which are not harmful to the human body, such as titanium and stainless steel. However, because calcium phosphate compounds, particularly hydroxyapatite, are much better in terms of biocompatibility, their use has been desired.

Under such circumstances, attempt has been made to combine calcium phosphate compounds with glass materials, metallic materials and synthetic resins, and some of the resultant composite bodies have been already put into practical use. However, when they are combined with the glass materials, there are problems that the glass elutes from the resultant composite bodies into the human body as time goes on, and that the composite bodies lack toughness.

The composite material of the calcium phosphate compound and the metallic material is obtained by charging the calcium phosphate compound particles into a metal frame or sintering a mixture of metal powder and the calcium phosphate compound powder. In the former case, however, the calcium phosphate compound is likely to move from the metal frame in the body. In the latter case, the calcium phosphate compound particles exposed on the surface of the sintered composite body are easily detached.

Though attempt has been made to blend a molten synthetic resin and calcium phosphate particles to provide their composite body, the calcium phosphate particles easily collapse during blending, and the molten synthetic resin easily covers the calcium phosphate particles in the course of molding the composite body. In addition, burring disadvantageously occurs during cutting.

Though attempt is also made to combine a composite body of calcium phosphate particles and cross-linked, synthetic resin particles with a highly biocompatible calcium phosphate block, the calcium phosphate block is easily detached. Also, because the calcium phosphate block is poor in toughness, it disadvantageously collapses in the course of molding.

OBJECT OF THE INVENTION

Therefore, an object of the present invention is to provide a calcium phosphate-synthetic resin composite body having excellent workability, impact resistance and water resistance as well as high biocompatibility Another object of the present invention is to provide a method for producing such a calcium phosphate-synthetic resin composite body.

DISCLOSURE OF THE INVENTION

As a result of an intensive study in view of the above object, the inventors have discovered that a calcium phosphate-synthetic resin composite body is provided with further improved workability, impact resistance, water resistance and biocompatibility, when a calcium phosphate block having extremely high biocompatibility is added to the calcium phosphate-synthetic resin composite body such that it is exposed on at least part of a surface of the composite body. The present invention has been completed based on this discovery.

Thus, the calcium phosphate-synthetic resin composite body of the present invention is produced by pressing a calcium phosphate block (or a calcium phosphate block and calcium phosphate particles), synthetic resin particles I, which are at least partially cross-linked in advance, and uncross-linked, synthetic resin particles II while heating, the calcium phosphate block being exposed on at least part of the surface of the composite body.

In the calcium phosphate-synthetic resin composite body of the present invention, the synthetic resin particles I are softened while retaining their shapes to some extent, whereas the uncross-linked, synthetic resin particles II having thermoplasticity are softened or melted during pressing while heating. When the calcium phosphate block is porous, the softened or molten synthetic resin particles preferably enter into pores of the calcium phosphate block. It is preferable that the calcium phosphate block is firmly fixed in the composite body by bonding the synthetic resin particles with the calcium phosphate block.

In the calcium phosphate-synthetic resin composite body, it is preferable that synthetic resin particles composed of the synthetic resin particles I, which are at least partially cross-linked in advance, and the uncross-linked, synthetic resin particles II are bonded to each other. By pressing while heating, the synthetic resin particles I are softened while retaining the shapes to some extent for bonding, and the synthetic resin particles II are softened or melted to enter voids between the particles. The synthetic resin particles II filling voids between the particles act as binders.

In a normal condition, not only are the calcium phosphate particles firmly fixed by the synthetic resin particles I and II, but also the synthetic resin particles I and II are firmly bonded to each other. At the time of cutting and polishing, however, exfoliation occurs at interfaces between the calcium phosphate particles and the synthetic resin particles and at interfaces between the synthetic resin particles I and II. Therefore, the calcium phosphate-synthetic resin composite body containing the calcium phosphate particles has excellent workability.

The calcium phosphate block is preferably porous in terms of biocompatibility. A calcium/phosphorus molar ratio in the calcium phosphate block is preferably 1.4 to 2.0. Also, preferably used from a practical standpoint is the sintered calcium phosphate block having a thickness of at least 1 mm.

The calcium phosphate particles are preferably porous in terms of biocompatibility. The average particle size of the calcium phosphate particles is preferably 0.001 to 10 mm, and the calcium/phosphorus molar ratio is preferably 1.4 to 2.0. The calcium phosphate particles are preferably sintered in advance.

Both of the synthetic resin particles I and II are preferably made of a water-insoluble acrylic or polystyrene resin, particularly polymethyl methacrylate. The content of the uncross-linked, synthetic resin particles II is preferably 0.2 to 50% by mass based on the sum of the synthetic resin particles I and II.

In the case of the composite body containing the calcium phosphate particles, the content of the calcium phosphate particles is preferably 80% or less by weight based on the sum of the calcium phosphate particles and the synthetic resin particles I and II.

The method for producing the calcium phosphate-synthetic resin composite body according to the present invention comprises the steps of (a) introducing a calcium phosphate block (or a calcium phosphate block and calcium phosphate particles), and synthetic resin particles I and II into a cavity of a forming die, such that the calcium phosphate block is present on at least part of a surface of the composite body, and such that the calcium phosphate particles, if any, are surrounded by the synthetic resin particles; and (b) by pressing them in the cavity of the forming die while heating, so that the synthetic resin particles are bonded to each other.

The calcium phosphate block (or the calcium phosphate block and the calcium phosphate particles) is preferably sintered. Its sintering temperature is preferably 500° C. to 1300° C.

DESCRIPTION OF THE PREFERRED EMBODIMENTS

[1] Calcium Phosphate-Synthetic Resin Composite Body

The calcium phosphate-synthetic resin composite body comprises a calcium phosphate block (or a calcium phosphate block and calcium phosphate particles), synthetic resin particles I, which are at least partially cross-linked in advance, and uncross-linked, synthetic resin particles II.

(1) Calcium Phosphate Block

The calcium/phosphorus molar ratio is preferably 1.4 to 2.0 in the calcium phosphate block. Specific examples of the calcium phosphate blocks include blocks of apatites such as hydroxyapatite and fluoroapatite, calcium phosphates such as tricalcium phosphate and tetracalcium phosphate, or mixtures thereof.

The calcium phosphate block may be porous or non-porous, though a porous one is more preferable. In the case of a porous calcium phosphate block, its porosity is preferably 5 to 80%. Though the pores of the calcium phosphate block may be of various sizes, they preferably have diameters of 20 to 2000 µm.

Though not particularly limited, the calcium phosphate block may be in a shape of a rectangular column or a circular cylinder. Though not particularly limited, the thickness of the calcium phosphate block is preferably 1 mm or more from a practical standpoint.

(2) Calcium Phosphate Particles

The calcium phosphate-synthetic resin composite body of the present invention may or may not contain the calcium phosphate particles. When containing the calcium phosphate particles, their composition is preferably the same as that of the calcium phosphate block. The calcium phosphate particles may be porous or non-porous particles, but porous ones are more preferable. In the case of porous calcium phosphate particles, their porosity is preferably 20 to 70%. Though the pores of the porous particles may be of various sizes, they preferably have diameters of 10 to 2000 µm.

It is preferable that the calcium phosphate particles have adjusted particle sizes so that their average particle diameter is 0.001 to 10 mm. The more preferable average particle diameter of the calcium phosphate particles is 0.01 to 6 mm. When the average particle diameter of the calcium phosphate particles is more than 10 mm, the calcium phosphate particles are easily detached from the calcium phosphate-synthetic resin composite body during use. On the other hand, when it is less than 0.001 mm, they are easily agglomerated with poor dispersibility and suffer from a high cost. The average particle diameter may be measured by known methods.

The calcium phosphate particles are preferably sintered before pressing and heating. The sintering temperature is preferably 500 to 1300° C. and more preferably 700 to 1200° C. When the sintering temperature is below 500° C., the calcium phosphate particles are easily collapsed. Particularly in the case of the porous calcium phosphate particles, they are deformed and lose their porosity due to the crushing of pores by the application of pressure. When the sintering temperature is above 1300° C., the calcium phosphate compound is undesirably decomposed or deteriorated.

A sintering time, in which the above sintering temperature is kept, is preferably 1 to 10 hours. When the sintering time is less than 1 hour, the calcium phosphate particles would not exhibit a sufficient reinforcing effect even if sintered. On the other hand, even when the sintering time is more than 10 hours, no further effect is obtained, only resulting in increase in cost. The more preferable sintering time is 2 to 5 hours. Though not particularly limited, a sintering atmosphere is preferably air to prevent the decomposition of the calcium phosphate particles.

(3) Synthetic Resin Particles

The synthetic resin particles comprise synthetic resin particles I, which are at least partially cross-linked in advance, and uncross-linked, synthetic resin particles II. The synthetic resin particles I, which are at least partially cross-linked in advance, and the uncross-linked, synthetic resin particles II are not limited as long as they are not harmful to the human body, and materials known in the art can be used therefor. The synthetic resin particles I and II preferably comprise a water-insoluble acrylic or polystyrene resin and the like, particularly polymethyl methacrylate. The same or different materials may be used for the synthetic resin particles I and II.

Each of the synthetic resin particles I and II has an average particle diameter of preferably 0.05 to 500 μm, more preferably 0.1 to 100 μm. Also, the average particle diameters of the synthetic resin particles are preferably smaller than that of the calcium phosphate particles.

The content of the synthetic resin particles II is preferably 0.2 to 50% by mass based on the sum of the synthetic resin particles I and II. When the content of the synthetic resin particles II is less than 0.2%, the composite body is not sufficiently stable in water. On the other hand, when their content is more than 50% by mass, not only are the synthetic resin particles II likely to intrude into the porous calcium phosphate particles at the step of pressing while heating, but also the resultant composite body has low workability.

(4) Structure of Calcium Phosphate-Synthetic Resin Composite Body

In the calcium phosphate-synthetic resin composite body of the present invention, the calcium phosphate block is exposed on at least part of its surface.

Figure 1A:
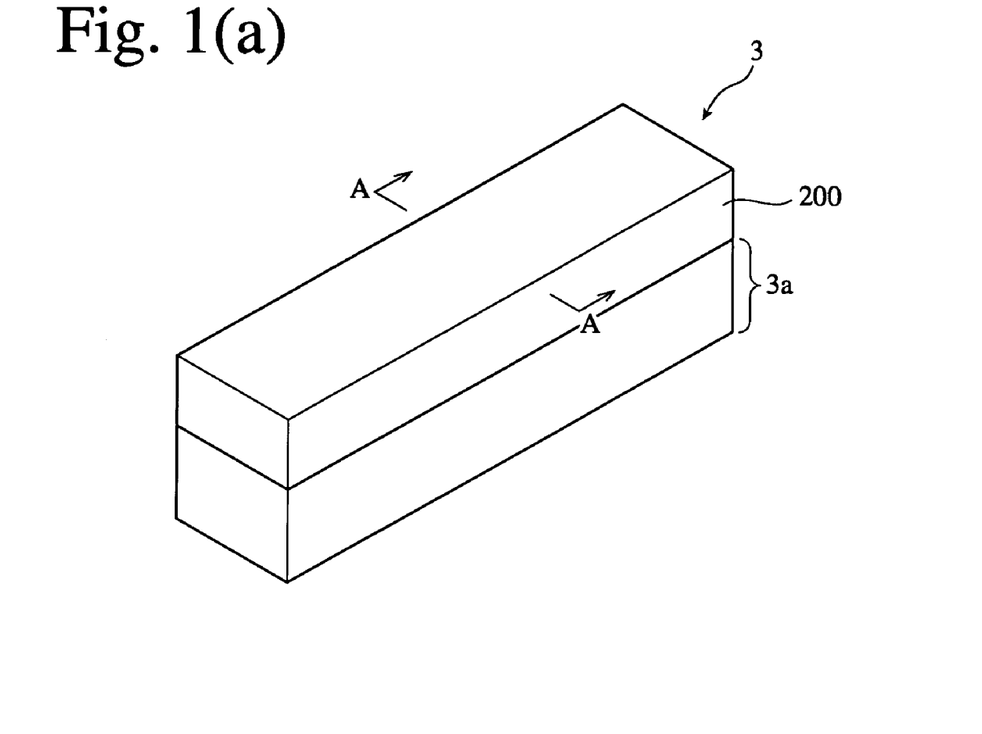
FIG. 1(a) is a perspective view showing the structure of the calcium phosphate-synthetic resin composite body according to one embodiment of the present invention.
Figure 1B:
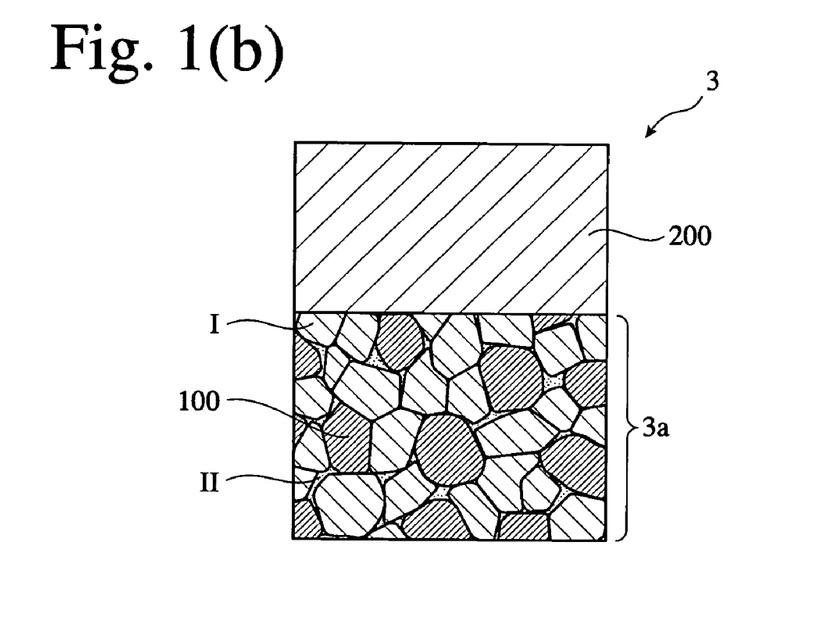
FIG. 1(b) is a vertical cross-sectional view showing the calcium phosphate-synthetic resin composite body of FIG. 1(a)
Figure 2A:
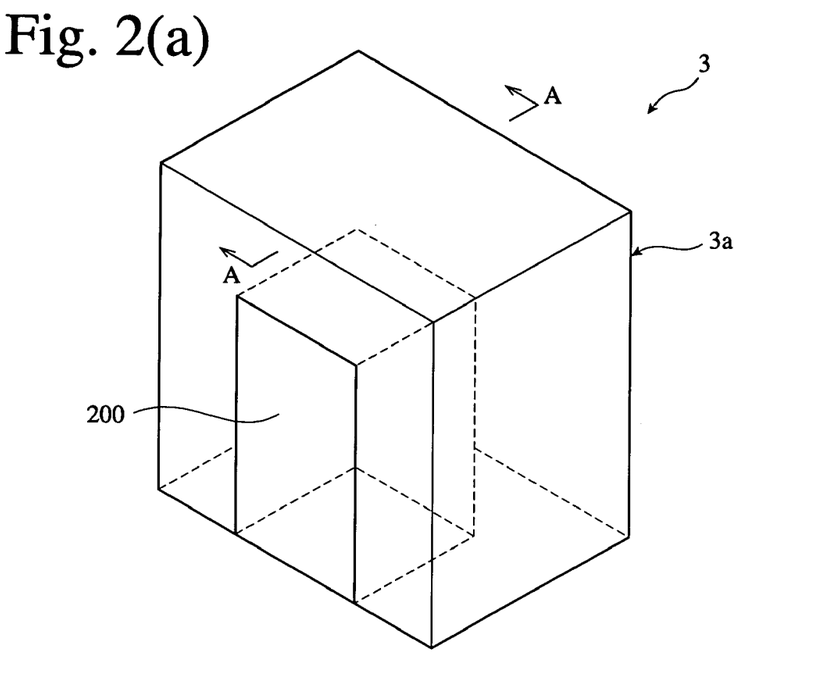
FIG. 2(a) is a perspective view showing the structure of the calcium phosphate-synthetic resin composite body according to another embodiment of the present invention.
Figure 2B:
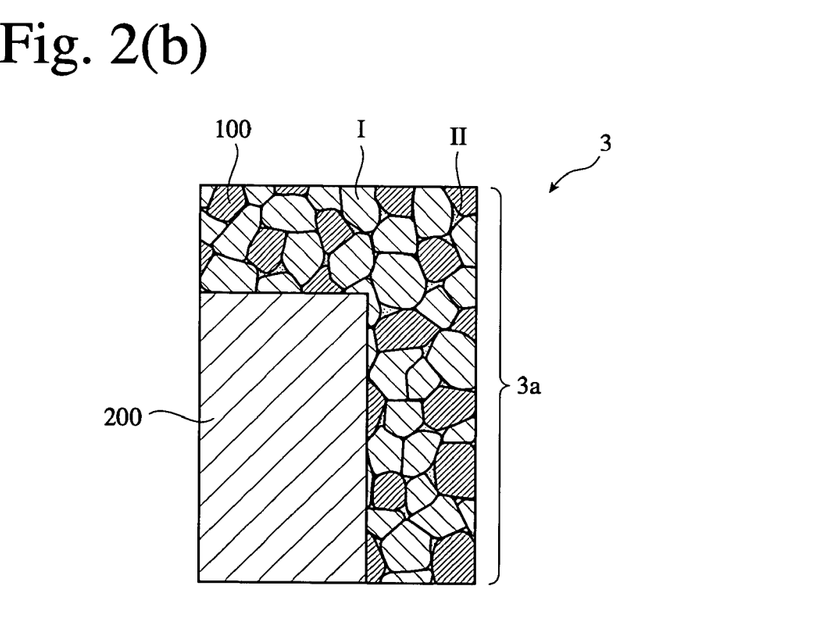
FIG. 2(b) is a vertical cross-sectional view showing the calcium phosphate-synthetic resin composite body of FIG. 2(a)
Figure 3A:
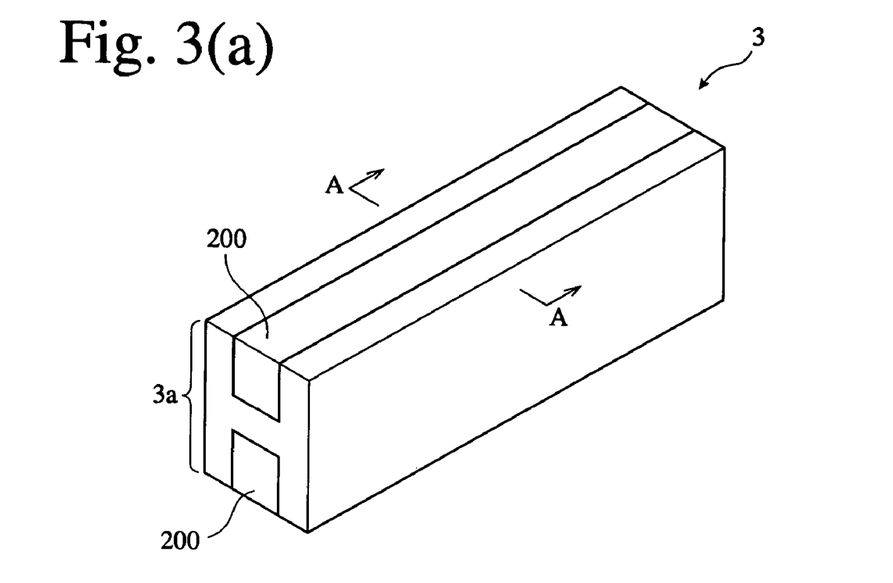
FIG. 3(a) is a perspective view showing the structure of the calcium phosphate-synthetic resin composite body according to a further embodiment of the present invention.
Figure 3B:
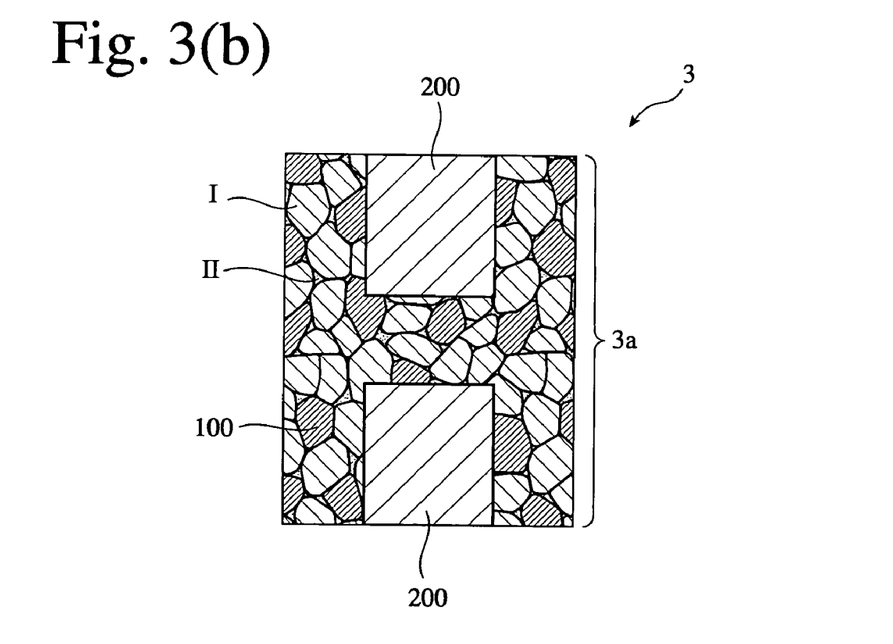
FIG. 3(b) is a vertical cross-sectional view showing the calcium phosphate-synthetic resin composite body of FIG. 3(a)
Figure 4A:
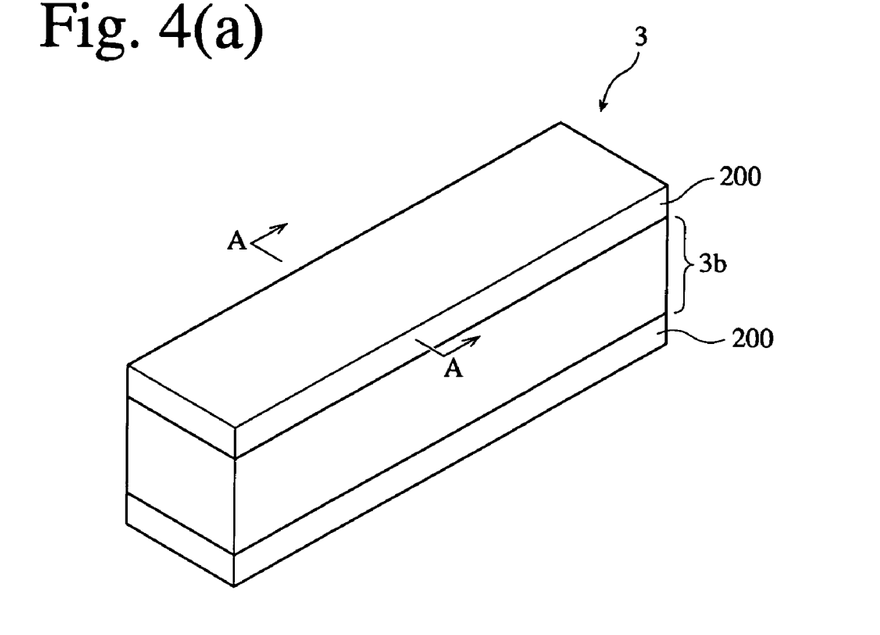
FIG. 4(a) is a perspective view showing the structure of the calcium phosphate-synthetic resin composite body according to a still further embodiment of the present invention.
Figure 4B:
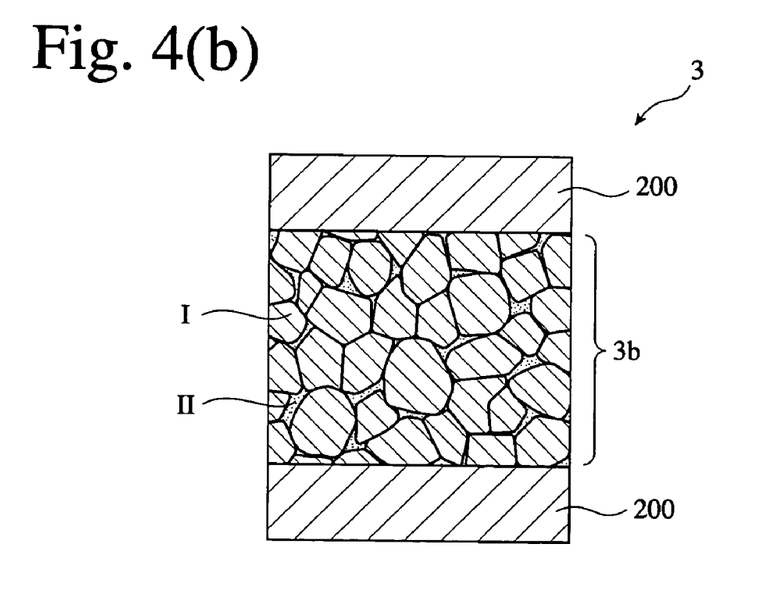
FIG. 4(b) is a vertical cross-sectional view showing the calcium phosphate-synthetic resin composite body of FIG. 4(a)
Figure 5A:
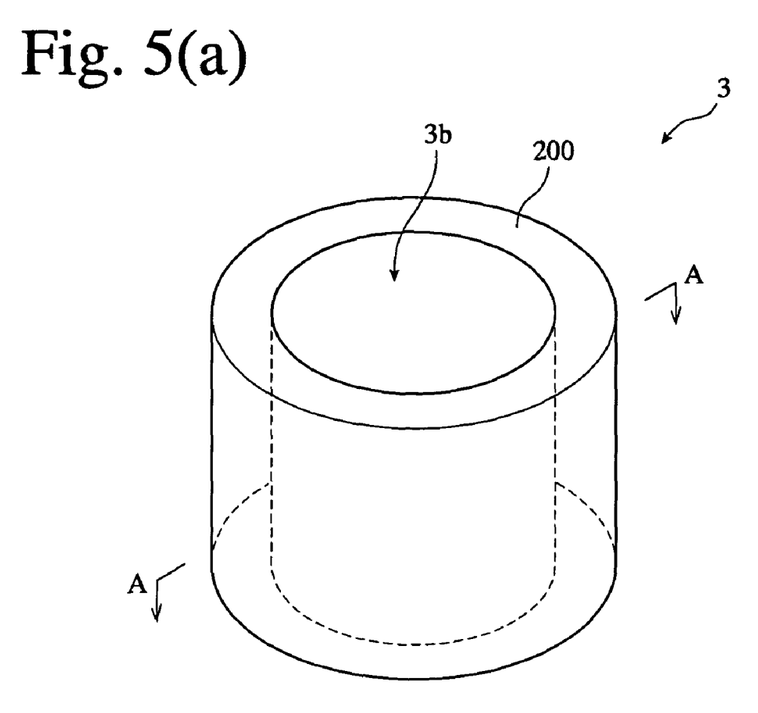
FIG. 5(a) is a perspective view showing the structure of the calcium phosphate-synthetic resin composite body according to a still further embodiment of the present invention.
Figure 5B:
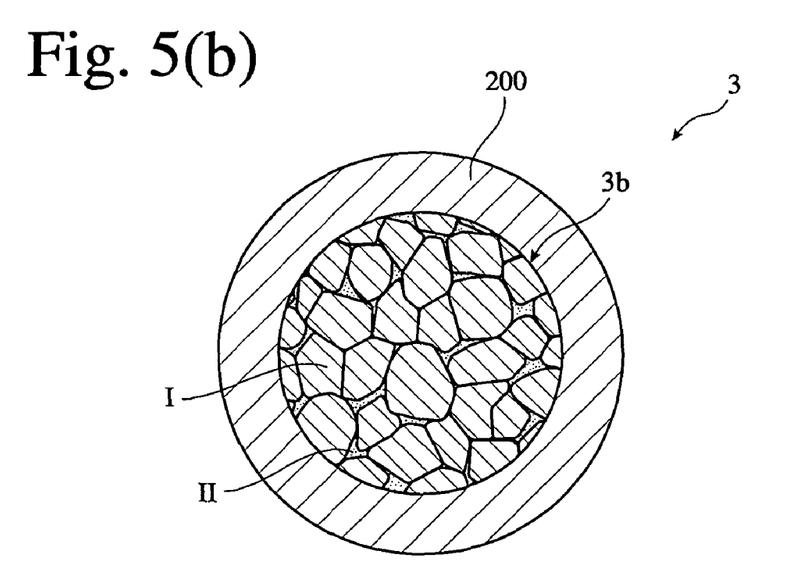
FIG. 5(b) is a vertical cross-sectional view showing the calcium phosphate-synthetic resin composite body of FIG. 5(a)

FIGS. 1–5 show the calcium phosphate-synthetic resin composite body 3 according to each embodiment of the present invention. In each figure, (a) is a perspective view showing the composite body 3, and (b) is a cross-sectional view taken along the line A—A in the perspective view. FIGS. 1–3 show examples of the calcium phosphate-synthetic resin composite body 3 containing the calcium phosphate particles 100, and FIGS. 4 and 5 show examples of the calcium phosphate-synthetic resin composite body 3 containing no calcium phosphate particles.

The calcium phosphate-synthetic resin composite body 3 shown in FIG. 1 has a double layer structure comprising the calcium phosphate block 200 and a layer 3a comprising a mixture of the calcium phosphate particles 100 and the synthetic resin particles. The synthetic resin particles in the layer 3a comprise the synthetic resin particles I, which are at least partially cross-linked in advance, and the uncross-linked, synthetic resin particles II. The cross-linked, synthetic resin particles I and the uncross-linked, synthetic resin particles II surround and tightly fix the calcium phosphate particles 100.

The calcium phosphate-synthetic resin composite body 3 shown in FIG. 2 has a structure in which the calcium phosphate block 200 is fit in part of the layer 3a comprising a mixture of the calcium phosphate particles 100 and the synthetic resin particles I and II. The calcium phosphate block 200 is exposed on two surfaces of the composite body 3. In other portions, this composite body is the same as the calcium phosphate-synthetic resin composite body 3 shown in FIG. 1.

The calcium phosphate-synthetic resin composite body 3 shown in FIG. 3 has a structure in which two calcium phosphate blocks 200, 200 are fit in center recesses of the layer 3a on upper and lower surfaces comprising a mixture of the calcium phosphate particles 100 and the synthetic resin particles I and II. The calcium phosphate blocks 200 are exposed on upper and lower surfaces of the composite body 3, and sandwich the layer 3a vertically and tightly fix the layer 3a. In other portions, this composite body is the same as the calcium phosphate-synthetic resin composite body 3 shown in FIG. 1.

The calcium phosphate-synthetic resin composite body 3 shown in FIG. 4 has a triple layer structure comprising a layer 3b made of the synthetic resin particles I, which are at least partially cross-linked in advance, the uncross-linked, synthetic resin particles II, and a pair of calcium phosphate blocks 200, 200 which tightly fix the layer 3b. In the synthetic resin particles in the layer 3b, the cross-linked, synthetic resin particles I and the uncross-linked, synthetic resin particles II are tightly bonded to one another.

The calcium phosphate-synthetic resin composite body 3 shown in FIG. 5 comprises a columnar layer 3b comprising synthetic resin particles I, which are at least partially cross-linked in advance, and uncross-linked, synthetic resin particles II, and a tubular calcium phosphate block 200 covering a side surface of the columnar layer 3b. In other portions, this composite body is the same as the calcium phosphate-synthetic resin composite body 3 shown in FIG. 4.

[2] Method for Producing Calcium Phosphate-Synthetic Resin Composite Body (1) Production of Calcium Phosphate Block The calcium phosphate block may be produced by using methods known in the art, but it is preferably produced according to the methods described in JP 2-167868 A and JP 8-48583 A, the disclosures of which are incorporated by reference herein in their entireties. The method for producing a calcium phosphate-synthetic resin composite body described in JP 2-167868 A is a method where a slurry or a fluid gel containing calcium phosphate compound power and a polymer material is foamed and then thickened or gelated, and the resultant foamed body is sintered if necessary. The method for producing a calcium phosphate-synthetic resin composite body described in JP 8-48583 A is a method where a mixture of calcium phosphate compound powder and a polymer material is formed into green compact by the application of pressure, and the resultant green compact is sintered.

(2) Production of Calcium Phosphate-Synthetic Resin Composite Body (I) Pressing/Heating Device The present invention utilizes a pressing/heating method to produce the calcium phosphate-synthetic resin composite body. The calcium phosphate-synthetic resin composite body may or may not contain calcium phosphate particles. Examples of the method for producing the composite body containing the calcium phosphate particles are described below. The composite body containing no calcium phosphate particles can also be obtained by a similar pressing/heating method.

Preferable pressing/heating methods for producing the calcium phosphate-synthetic resin composite body include a method where the calcium phosphate block and a mixture comprising the calcium phosphate particles, the synthetic resin particles I, which are at least partially cross-linked in advance, and the uncross-linked, synthetic resin particles II are charged between a pair of molds connected to a heat source, which are heated while applying pressure. The pressing/heating are preferably carried out in vacuum, or in an atmosphere of an inert gas such as $N_2$, He and Ar.

Figure 6:
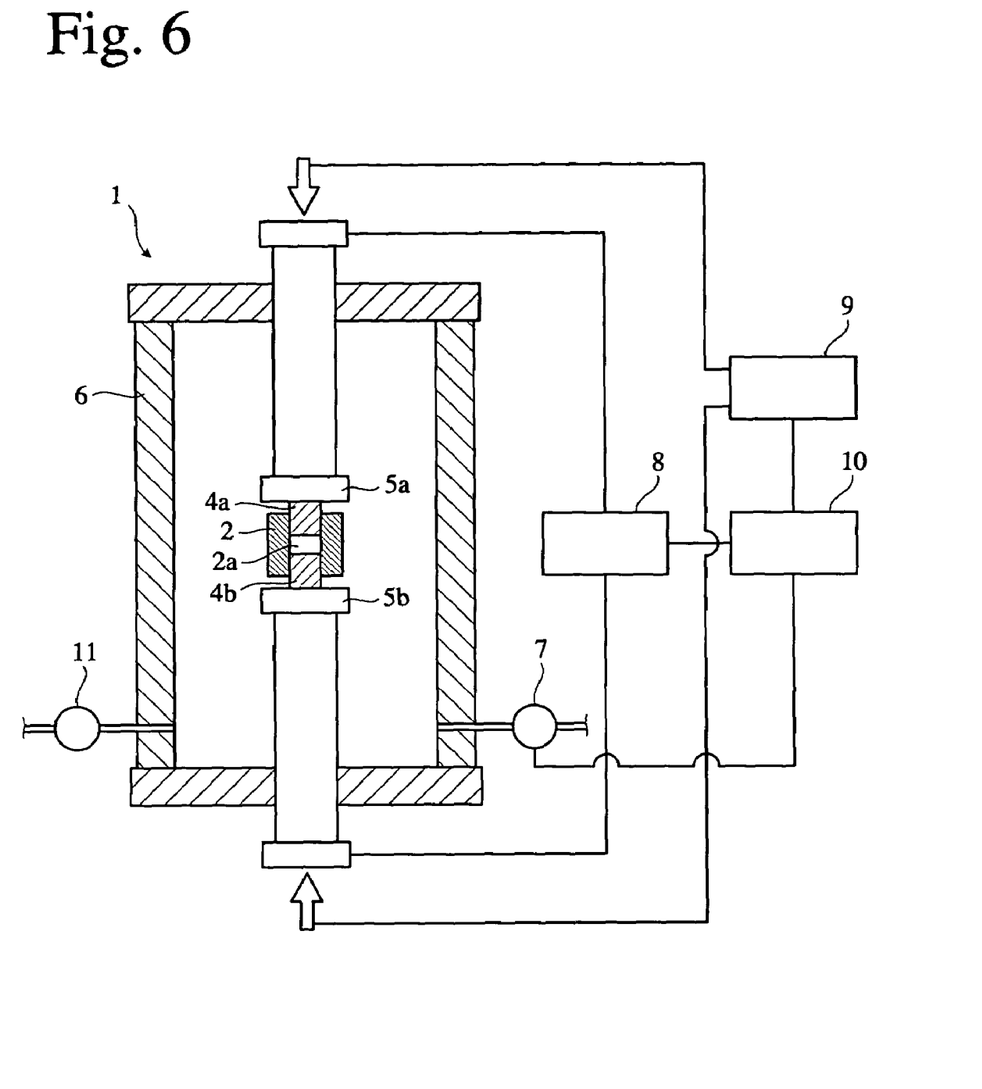
FIG. 6 is a schematic view showing the structure of the vacuum pressing/heating device for carrying out the method of the present invention.
Figure 7:
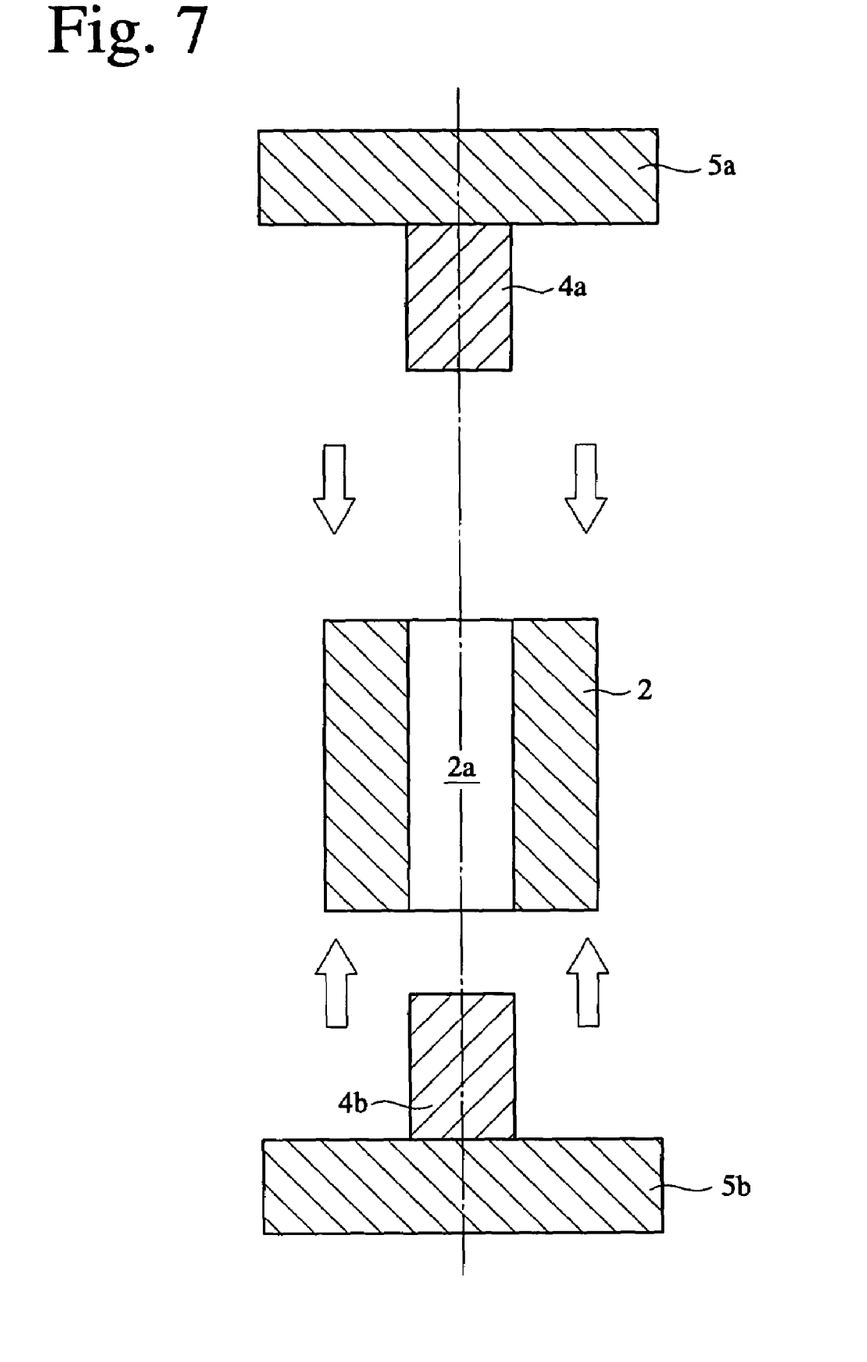
FIG. 7 is an exploded view showing the forming portion of the vacuum pressing/heating device.
Figure 8:
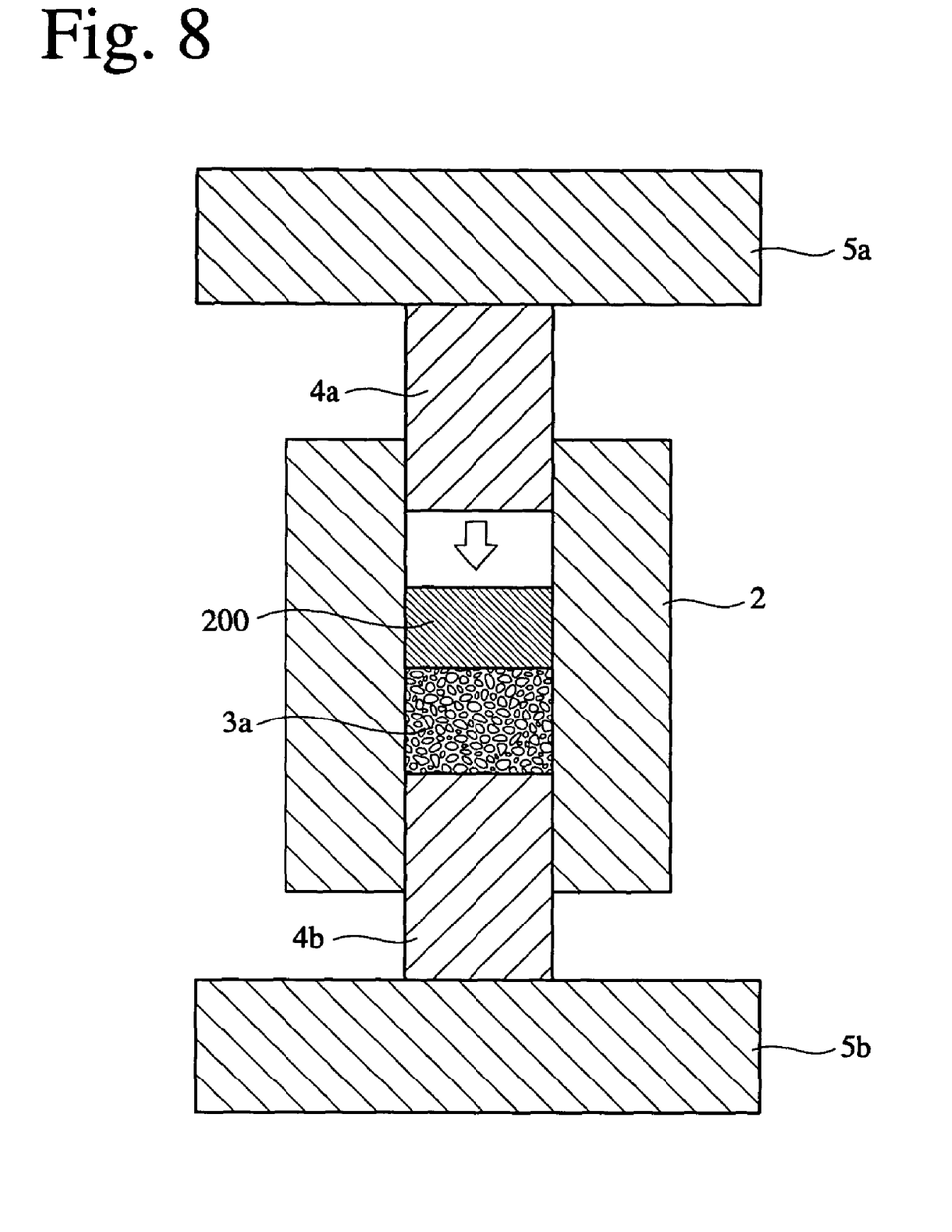
FIG. 8 is a vertical cross-sectional view showing a state in which a calcium phosphate block and a mixture of calcium phosphate particles and synthetic resin particles I and II are charged into a cavity of a forming die of a vacuum pressing/heating device.

FIGS. 6–8 show examples of the devices in which the pressing/heating are carried out in vacuum or in an inert gas atmosphere. In FIG. 6, the pressing/heating device 1 has a vacuum chamber 6 provided with a vacuum pump 7, a forming die 2 disposed therein, a pair of punches 4a and 4b for pressing while heating the calcium phosphate block and the mixture 3a comprising the calcium phosphate particles and the synthetic resin particles I and II introduced into a cavity 2a of the forming die 2, and rams 5a and 5b for driving the punches 4a and 4b. A thermocouple (not shown) for measuring the treatment temperature is embedded in the forming die 2. Also, a gas pump 11 comprises an inlet and a gas container (not shown).

Each ram 5a and 5b is driven by a press-driving mechanism 9 to press the mixture 3a while heating each punch 4a and 4b, with electric power received from a power supply 8 connected via a terminal (not shown). A control means 10 is connected to the press-driving mechanism 9, the power supply 8, the vacuum pump 7 and the thermocouple to control pressure and a heating temperature in the cavity 2a of the forming die 2 and a degree of vacuum in the vacuum chamber 6.

As is shown in FIG. 7, the forming die 2 has an annular structure having a cavity 2a having a circular, oval or rectangular cross section. Each punch 4a and 4b has a slightly smaller cross section than the cavity 2a such that it can move up and down in the cavity 2a of the forming die 2. The punches 4a and 4b are secured to the rams 5a and 5b, respectively.

(II) Filling

The calcium phosphate block and the mixture 3a are charged into the cavity 2a of the forming die 2 such that the calcium phosphate block is exposed on at least part of the surface of the resultant composite body, and that the synthetic resin particles I and II surround the calcium phosphate particles.

The content of the calcium phosphate particles is preferably 80% or less by weight based on the sum of the synthetic resin particles I and II and the calcium phosphate particles. When the content of the calcium phosphate particles is more than 80% by mass, the calcium phosphate particles are not fully covered with the synthetic resin particles, resulting in easy detachment of the calcium phosphate particles.

(III) Pressing and Heating Treatment

As is shown in FIG. 8, the calcium phosphate block and the mixture 3a are charged into the cavity 2a, and the vacuum chamber 6 is sealed and evacuated by the vacuum pump 7 to a degree of vacuum of about 1 Pa. Thereafter, an inert gas such as $N_2$, He or Ar may be introduced. This treatment provides an oxide-decreased (low-concentration oxide) condition, thereby preventing the oxidative degradation of the synthetic resin.

When the press-driving mechanism 9 is operated by the control means 10, at least one of the rams 5a and 5b moves in a direction to approach one another, so that the punches 4a and 4b secured thereto press the mixture 3a. The pressing power of the punches 4a and 4b is preferably 0.5 to 50 MPa, and more preferably 1.0 to 20 MPa. When the pressing power is less than 0.5 MPa, sufficient adhesion is not achieved between the synthetic resin particles and the calcium phosphate block, and the synthetic resin particles themselves, resulting in easy detachment of the calcium phosphate block and the calcium phosphate particles from the composite body. Even if it is more than 50 MPa, correspondingly improved shape retention is not obtained, rather resulting in problems such as the collapse of the calcium phosphate block and the calcium phosphate particles.

The punches 4a and 4b are heated by the power supply 8 to heat the mixture 3a under pressure. The mixture 3a is preferably heated according to a predetermined temperature elevation program. In that case, the temperature of the mixture 3a is detected by a thermocouple (not shown) disposed in the forming die 2, and an output of the thermocouple is sent to the control means 10. The control means 10 produces a signal for temperature elevation according to the temperature elevation program on the basis of input temperature data, and sends it to the power supply 8. The power supply 8 supplies appropriate current to the rams 5a and 5b according to a command from the control means 10.

The heating temperature is preferably 130° C. to 300° C., and more preferably 150° C. to 250° C. When the heating temperature is lower than 130° C., sufficient adhesion is not achieved between the synthetic resin particles themselves, the synthetic resin particles and the calcium phosphate block, and the synthetic resin particles and the calcium phosphate particles, resulting in easy detachment of the calcium phosphate block and the calcium phosphate particles from the composite body. The heating temperature higher than 300° C. is not preferable, because the synthetic resin particles cannot retain their shapes, sometimes resulting in integration by melting.

The heating time (time period in which the heating temperature is kept) is preferably 1 to 30 minutes. When the heating time is shorter than one minute, sufficient adhesion is not achieved between the synthetic resin particles themselves, the synthetic resin particles and the calcium phosphate block, and the synthetic resin particles and the calcium phosphate particles. The heating time longer than 30 minutes is not preferable, because it would not provide improved adhesion. A more preferable heating time is 3 to 10 minutes.

After the pressing/heating treatment, the calcium phosphate-synthetic resin composite body is cooled to room temperature, and removed from the cavity of the forming die. When the calcium phosphate particles are not exposed sufficiently on the surface of the composite body, the surface may be ground.

The present invention will be explained in more detail by the following Examples without intention to limit the present invention thereto.

EXAMPLE 1

10 g of calcium phosphate powder having an average particle diameter of 30 μm was added to 20 g of an aqueous solution containing 1% by mass of methyl cellulose, and blended at a predetermined speed for a predetermined period of time. The resultant foamed slurry was molded in a forming die frame, dried at 80° C. for 72 hours and then sintered in an air furnace at 900° C. for 4 hours. Machining was carried out to provide a calcium phosphate block 200 having a calcium/phosphorus molar ratio of 1.67, an outer shape of 8 mm×25 mm×3 mm in thickness and a porosity of 30%.

0.50 g of porous calcium phosphate particles having particle diameters of 0.2 to 0.6 mm and a calcium/phosphorus molar ratio of 1.67, which was sintered in an air furnace at 900° C., 1.35 g of cross-linked acrylic powder I having an average particle diameter of 15.0 µm (Chemisnow MX-1500H manufactured by Soken Chemical & Engineering Co., Ltd.), and 0.15 g of uncross-linked acrylic powder II having an average particle diameter of 1.5 µm (Chemisnow MP-1400 manufactured by Soken Chemical & Engineering Co., Ltd.) were mixed to produce a mixture 3a having the acrylic powder surrounding the calcium phosphate particles, and charged into a cavity 2a (8 mm×25 mm×50 mm in height) of a forming die 2 of a pressing/heating device. The calcium phosphate block 200 was disposed on the mixture 3a filled in the die with its thickness directed along the height of the cavity 2a of the forming die 2.

The mixture 3a of the porous calcium phosphate particles and the synthetic resin particles and the porous calcium phosphate block 200 both charged into the cavity 2a of the forming die 200 as described above were kept at a heating temperature of 250° C. for 5 minutes while pressing at a pressure of 5 MPa from upper and lower sides. Subsequently, they were cooled, and the pressure was released at room temperature.

The resultant calcium phosphate-synthetic resin composite body was machined by a milling cutter to a shape of 8 mm×25 mm×8 mm in thickness as shown in FIG. 1. The observation of a surface of a layer comprising the calcium phosphate particles and the synthetic resin particles in the composite body by a scanning electron microscope revealed that calcium phosphate was well exposed on the surface without being covered with the acrylic resin. The calcium phosphate-synthetic resin composite body had a three-point flexural strength of 25.6 MPa. The three-point flexural strength was measured with the laminate direction of the composite body layer aligned horizontally in a measuring device.

EXAMPLE 2

A foamed slurry was prepared in the same manner as in Example 1, except for changing the blending speed and time of a mixture of an aqueous methyl cellulose solution and calcium phosphate powder to change the porosity of the resultant green body. The foamed slurry was poured into a foaming die frame, molded, dried at 80° C. for 72 hours and then machined. The resultant two green bodies were then sintered in an air furnace at 1000° C. for 4 hours, resulting in two calcium phosphate blocks 200, 200 each having a width of 6 mm, a length of 25 mm and a thickness of 3 mm, which had a calcium/phosphorus molar ratio of 1.67 and a porosity of 10%.

One of the above two calcium phosphate blocks 200, 200 was placed at a center bottom of a cavity 2a (8 mm×25 mm×50 mm in height) of a forming die 2 in a pressing/heating device, such that its thickness was aligned with the height of the cavity 2a of the forming die 2. Next, 1.00 g of porous calcium phosphate particles having an average particle diameter of 0.01 mm and a calcium/phosphorus molar ratio of 1.67, which were sintered in an air furnace at 1000° C., 0.998 g of cross-linked acrylic powder I having an average particle diameter of 90.0 µm (Chemisnow MR-90G manufactured by Soken Chemical & Engineering Co., Ltd.), and 0.002 g of uncross-linked acrylic powder II having an average particle diameter of 1.5 µm (Chemisnow MP-1400 manufactured by Soken Chemical & Engineering Co., Ltd.) were mixed to produce a mixture 3a having the acrylic powder surrounding the calcium phosphate particles, and poured onto the calcium phosphate block 200 in the cavity 2a.

With another calcium phosphate block 200 placed on the mixture 3a of the porous calcium phosphate particles and the synthetic resin particles as shown in FIG. 3, the mixture 3a and a pair of the porous calcium phosphate blocks 200, 200 in the cavity 2a of the forming die 2 were kept at a heating temperature of 250° C. for 5 minutes while pressing at a pressure of 20 MPa from upper and lower sides. Subsequently, they were cooled, and the pressure was released at room temperature.

The resultant calcium phosphate-synthetic resin composite body was machined by a milling cutter to a shape of 8 mm×25 mm×8 mm in thickness as shown in FIG. 3. The observation of a surface of a layer comprising the calcium phosphate particles and the synthetic resin particles in the composite body by a scanning electron microscope revealed that calcium phosphate was well exposed on the surface without being covered with the acrylic resin. The calcium phosphate-synthetic resin composite body had a three-point flexural strength of 38.1 MPa. The measurement of the three-point flexural strength was carried out, with the composite body arranged such that a surface on which the calcium phosphate block was not exposed was directed vertically in a measuring device.

EXAMPLE 3

Two calcium phosphate blocks 200, 200 each having a calcium/phosphorus molar ratio of 1.50, an outer shape of 8 mm×25 mm×1.5 mm in thickness and a porosity of 55%, which were sintered in an air furnace at 1200° C. for 4 hours, were produced in the same manner as in Example 2 except for changing a calcium/phosphorus molar ratio and the blending speed and time of the foamed slurry to change the porosity of the resultant green body.

One of the above calcium phosphate blocks 200, 200 was placed in a cavity 2a (8 mm×25 mm×50 mm in height) of a forming die 2 in a pressing/heating device, such that the calcium phosphate block 200 was arranged at the bottom of the cavity 2a with its thickness aligned with the height of the cavity 2a f the forming die 2. Next, 1.00 g of porous calcium phosphate particles having particle diameters of 0.2 to 0.3 mm and a calcium/phosphorus molar ratio of 1.50, which were sintered in an air furnace at 1200° C., 0.98 g of cross-linked acrylic powder I having an average particle diameter of 15.0 µm (Chemisnow MX-1500H manufactured by Soken Chemical & Engineering Co., Ltd.), and 0.02 g of uncross-linked acrylic powder II having an average particle diameter of 1.5 µm (Chemisnow MP-1400 manufactured by Soken Chemical & Engineering Co., Ltd.) were mixed to produce a mixture 3a having the acrylic powder surrounding the calcium phosphate particles, and placed above the calcium phosphate block 200. Another calcium phosphate block 200 was then arranged on the charged mixture 3a with its thickness direction aligned with the height of the cavity 2a of the forming die 2.

The mixture 3a of the synthetic resin particles and the two porous calcium phosphate block 200, 200 thus charged into the cavity 2a of the forming die 2 were kept at a heating temperature of 200° C. for 5 minutes while pressing at a pressure of 10 MPa from upper and lower sides. Subsequently, they were cooled, and the pressure was released at room temperature.

The resultant calcium phosphate-synthetic resin composite body was machined by a milling cutter to a shape of 8 mm×25 mm×8.1 mm in thickness as shown in FIG. 4. The composite body had a three-point flexural strength of 28.6 MPa. The measurement of the three-point flexural strength was carried out with the laminate direction of the composite body layer aligned horizontally in a measuring device.

EXAMPLE 4

2.00 g of porous calcium phosphate particles having particle diameters of 0.2 to 0.6 mm and a calcium/phosphorus molar ratio of 2.00, which were sintered in an air furnace at 1000° C., 1.00 g of cross-linked acrylic powder I having an average particle diameter of 15.0 µm (Chemisnow MX-1500H manufactured by Soken Chemical & Engineering Co., Ltd.), and 1.00 g of uncross-linked acrylic powder II having an average particle diameter of 0.4 µm (Chemisnow MP-1000 manufactured by Soken Chemical & Engineering Co., Ltd.) were mixed to produce a mixture 3a having the acrylic powder surrounding the calcium phosphate particles, and charged into a forming die having an internal diameter of 9 mm and a height of 60 mm in a pressing/heating device.

The mixture 3a of the porous calcium phosphate particles and the synthetic resin particles thus charged was kept at a heating temperature of 150° C. for 5 minutes while pressing at a pressure of 5 MPa from upper and lower sides. Subsequently, they were cooled, and the pressure was released at room temperature. The resultant calcium phosphate particles-synthetic resin composite body was machined by a lathe to obtain a composite body block having an outer diameter of 6.9 mm and a height of 27 mm.

A tubular compact body made of the same calcium phosphate as in Example 1 was sintered in an air furnace at 1000° C. for 2 hours to produce a tubular calcium phosphate block 200 with an outer shape having an external diameter of 10 mm, an internal diameter of 7 mm and a height of 25 mm, which had a porosity of 40% and a calcium/phosphorus molar ratio of 2.00.

The tubular porous calcium phosphate block 200 was first placed in a cavity 2a (10 mm in internal diameter and 60 mm in height) of a forming die 2 in a pressing/heating device, and the calcium phosphate particles-synthetic resin composite body block having an outer diameter of 6.9 mm and a height of 27 mm was then charged into the tubular calcium phosphate block 200.

With the tubular porous calcium phosphate block 200 filled with the block 3a comprising the porous calcium phosphate particles and the synthetic resin particles as described above, all of them were kept at a heating temperature of 250° C. for 10 minutes while pressing at a pressure of 10 MPa from upper and lower sides. Subsequently, they were cooled, and the pressure was released at room temperature.

The resultant composite body was machined by a lathe to a shape of 10 mm in external diameter and 25 mm in height as shown in FIG. 5. The composite body had a three-point flexural strength of 31.0 MPa. The measurement of the three-point flexural strength was carried out with the laminate direction of the composite body layer aligned vertically in a measuring device.

As described above, the calcium phosphate-synthetic resin composite body of the present invention has excellent biocompatibility since a calcium phosphate block having extremely high biocompatibility is exposed on at least part of a surface of the composite body. The calcium phosphate-synthetic resin composite body of the present invention having such a structure is suitable for artificial dental roots, bone reinforcements, etc. The present disclosure relates to subject matter contained in Japanese Patent Application No. 2002-200085 (filed on Jul. 9, 2002) which is expressly incorporated herein by reference in its entirety.

What is claimed is:

1. A calcium phosphate-synthetic resin composite body produced by pressing a calcium phosphate block, calcium phosphate particles, and synthetic resin particles I, which are at least partially cross-linked in advance, and uncross-linked, synthetic resin particles II while heating, said calcium phosphate block being exposed on at least part of the surface of said composite body.

2. The calcium phosphate-synthetic resin composite body as set forth in claim 1, wherein the content of said calcium phosphate particles is 80% or less by weight based on the sum of said synthetic resin particles I and II and said calcium phosphate particles.

3. The calcium phosphate-synthetic resin composite body as set forth in claim 1, wherein said synthetic resin particles are bonded to each other by softening or melting during pressing while heating.

4. The calcium phosphate-synthetic resin composite body as set forth in claim 1, wherein said synthetic resin particles I and II are made of a water-insoluble acrylic or polystyrene resin.

5. The calcium phosphate-synthetic resin composite body as set forth in claim 1, wherein said calcium phosphate block and/or said calcium phosphate particles are sintered.

6. The calcium phosphate-synthetic resin composite body as set forth in claim 1, wherein said calcium phosphate block and said calcium phosphate particles are porous.

7. The calcium phosphate-synthetic resin composite body as set forth in claim 1, wherein said calcium phosphate block has a thickness of 1 mm or more.

8. The calcium phosphate-synthetic resin composite body as set forth in claim 1, wherein the content of said synthetic resin II is 0.2 to 50% by mass based on the sum of said synthetic resin particles I and II.

9. The calcium phosphate-synthetic resin composite body as set forth in claim 1, wherein a calcium/phosphorus molar ratio in said calcium phosphate block and said calcium phosphate particles is 1.4 to 2.0.

10. The calcium phosphate-synthetic resin composite body as set forth in claim 1, wherein said calcium phosphate particles have an average particle size of 0.001 to 10 mm.

11. A calcium phosphate-synthetic resin composite body produced by pressing a calcium phosphate block, synthetic resin particles I, which are at least partially cross-linked in advance, and uncross-linked, synthetic resin particles II while heating, said calcium phosphate block being exposed on at least part of the surface of said composite body.

12. The calcium phosphate-synthetic resin composite body as set forth in claim 11, wherein said synthetic resin particles are bonded to each other.

13. The calcium phosphate-synthetic resin composite body as set forth in claim 11, wherein said synthetic resin particles I and II are made of a water-insoluble acrylic or polystyrene resin.

14. The calcium phosphate-synthetic resin composite body as set forth in claim 11, wherein said calcium phosphate block is sintered.

15. The calcium phosphate-synthetic resin composite body as set forth in claim 11, wherein said calcium phosphate block is porous.

16. The calcium phosphate-synthetic resin composite body as set forth in claim 11, wherein said calcium phosphate block has a thickness of 1 mm or more.

17. The calcium phosphate-synthetic resin composite body as set forth in claim 11, wherein the content of said synthetic resin particles II is 0.2 to 50% by mass based on the sum of said synthetic resin particles I and II.

18. The calcium phosphate-synthetic resin composite body as set forth in claim 11, wherein a calcium/phosphorus molar ratio in said calcium phosphate block is 1.4 to 2.0.

19. A method for producing the calcium phosphate-synthetic resin composite body as set forth in claim 1 comprising the steps of (a) introducing said calcium phosphate block, said calcium phosphate particles, said synthetic resin particles I and II into a cavity of a forming die such that said calcium phosphate block is present on at least part of the surface of said composite body, and that said synthetic resin particles surround said calcium phosphate particles; and (b) pressing them in said forming die cavity while heating, so that said synthetic resin particles are bonded to each other.

20. A method for producing the calcium phosphate-synthetic resin composite body as set forth in claim 11, comprising (c) introducing said calcium phosphate block and synthetic resin particles I and II into a cavity of a forming die, such that said calcium phosphate block is present on at least part of the surface of said body; and (d) pressing them in said forming die cavity while heating, so that said synthetic resin particles are bonded to each other.

21. The method for producing the calcium phosphate-synthetic resin composite body as set forth in claim 19 further comprising sintering said calcium phosphate block.

22. The method for producing the calcium phosphate-synthetic resin composite body as set forth in claim 20 further comprising sintering said calcium phosphate block.

23. The method for producing the calcium phosphate-synthetic resin composite body as set forth in claim 21, wherein the sintering temperature of said calcium phosphate block is 500° C. to 1300° C.

24. The method for producing the calcium phosphate-synthetic resin composite body as set forth in claim 22, wherein the sintering temperature of said calcium phosphate block is 500° C. to 1300° C.

25. The method for producing the calcium phosphate-synthetic resin composite body as set forth in claim 19 further comprising sintering said calcium phosphate block and said calcium phosphate particles.

26. The method for producing the calcium phosphate-synthetic resin composite body as set forth in claim 25, wherein the sintering temperature of said calcium phosphate block and said calcium phosphate particles is 500° C. to 1300° C.

* * * * *